(12) United States Patent
Oda et al.

(10) Patent No.: US 7,867,722 B2
(45) Date of Patent: Jan. 11, 2011

(54) **PRETREATMENT AGENT FOR *LIMULUS* TEST**

(75) Inventors: Toshio Oda, Higashiyamato (JP); Jun Aketagawa, Higashiyamato (JP)

(73) Assignee: Seikagaku Corporation, Tokyo (JP)

( * ) Notice: Subject to any disclaimer, the term of this patent is extended or adjusted under 35 U.S.C. 154(b) by 50 days.

(21) Appl. No.: 11/814,949

(22) PCT Filed: Jan. 27, 2006

(86) PCT No.: PCT/JP2006/301339

§ 371 (c)(1),
(2), (4) Date: Jul. 27, 2007

(87) PCT Pub. No.: WO2006/080448

PCT Pub. Date: Aug. 3, 2006

(65) Prior Publication Data

US 2009/0011448 A1  Jan. 8, 2009

(30) Foreign Application Priority Data

Jan. 27, 2005 (JP) ............................. 2005-020444
Jan. 27, 2005 (JP) ............................. 2005-020445

(51) Int. Cl.
*G01N 33/53* (2006.01)
*C09N 3/00* (2006.01)

(52) U.S. Cl. .................................... 435/7.2; 252/183.14

(58) Field of Classification Search ........................ None
See application file for complete search history.

(56) References Cited

U.S. PATENT DOCUMENTS 5,286,625 A * 2/1994 Tanaka et al. ................. 435/18
5,695,948 A   12/1997 Tanaka et al.

FOREIGN PATENT DOCUMENTS

| EP | 0 588 303 A1 | 3/1994 |
| EP | 0 649 021 A1 | 4/1995 |
| JP | 6-70796 A | 3/1994 |
| JP | 07-128337 A | 5/1995 |
| JP | 08-75751 A | 3/1996 |
| JP | 10-293129 A | 11/1998 |

OTHER PUBLICATIONS

Odabasi et al. Beta-D-Glucan as a Dignostic Adjunct for Invasive Fungal Infections: Validation, Cutoff Development, and Performance in Patients With Acute Myelogenic Leukemia and Myelodysplastic Syndrome; Clinical Infectious Diseases, vol. 39 (2004) 199-205.*
Fungitell Product Insert, Glucan Assay for (1,3)-Beta-D-Glucan in Serum; Oct. 2004, downloaded from http://web.archive.org/web/20050128221519/http.acciusa.com/pdfs/fungitell_insert.pdf on Jun. 24, 2009.*

* cited by examiner

*Primary Examiner*—Rebecca E. Prouty
*Assistant Examiner*—Paul C. Martin
(74) *Attorney, Agent, or Firm*—Sughrue Mion, PLLC

(57) ABSTRACT

A pretreatment agent for a sample to be subjected to *Limulus* assay comprising an alkali metal sulfate and/or an alkaline earth metal sulfate wherein the sulfate(s) has a final concentration of 20 mM or more when the sulfate(s) is allowed to contact with the sample, or an alkali metal halide and/or an alkaline earth metal halide wherein the halide(s) has a final concentration of from 0.4 M to 1.2 M or less when the halide(s) is allowed to contact with the sample, or a kit for *Limulus* assay reagent comprising thereof as a composing article.

2 Claims, No Drawings

PRETREATMENT AGENT FOR *LIMULUS* TEST

TECHNICAL FIELD

The present invention relates to a pretreatment agent for *Limulus* assay use, a *Limulus* reagent kit which comprises it as a composing article and the like.

BACKGROUND OF THE INVENTION

The following abbreviations are used in the application documents of the present application.

BG: (1→3)-β-D-glucan

EDTA: ethylenediamintetraacetic acid

PBS: phosphate buffered saline

Background arts of the present invention are described in the following.

It is described in Patent Reference 1 that a method for measuring BG, which comprises pre-treating a sample which may contain a BG mainly consisting of a triple helix structure, under a strong alkaline condition, to destroy or inactivate endotoxin alone or endotoxin and a factor G system reaction disturbing factor, which are possibly contained in the sample as reaction disturbing factors, followed by subjecting it to a *Limulus* reaction by a *Limulus* reagent. Additionally, it is described in "Example 3" of said reference that schizophyllan consisting of 100% triple helix structure is added to PBS (+) and Hanks' solution prior to the *Limulus* assay, and that each of 0.492 mM MgSO$_4$ and 0.812 mM MgSO$_4$ is contained in said PBS (+) and Hanks' solution.

Additionally, it is described in Patent Reference 2 that an alkaline earth metal halide in a pretreatment agent for endotoxin assay use is set to a range of from 0.005 to 0.05 mol/L, and an alkali metal halide is set to a range of from 0.05 to 0.5 mol/L. However, the concentration disclosed therein is concentration "in a pretreatment agent" and is not the final concentration when it is allowed to contact with a sample.

There is no description or suggestion in any of these references on a pretreatment in which an alkali metal sulfate and/or an alkaline earth metal sulfate is allowed to contact with a sample which is subjected to a *Limulus* assay, under such a condition that its final concentration becomes 20 mM or more.

Additionally, there is no description or suggestion also on a pretreatment in which an alkali metal halide and/or an alkaline earth metal halide is allowed to contact with a sample which is subjected to a *Limulus* assay, under such a condition that its final concentration becomes more than 0.4 M and equal to or lower than 1.2 M.

Patent Reference 1: JP-A-7-128337

Patent Reference 2: JP-A-6-70796

DISCLOSURE OF THE INVENTION

Problems to be Solved by the Invention

An object of the present invention is providing a means for effectively inhibiting nonspecific reactions in a *Limulus* assay. The term "nonspecific reactions in a *Limulus* assay" as used herein means all reactions which are caused by factors other than the subject substances of the *Limulus* assay (endotoxin, BG and the like) and affect on the results of *Limulus* assay. Accordingly, for example, insolubilization of components in a sample to be subjected to the *Limulus* assay, components in the pretreatment agent, components in the *Limulus* reagent and the like substances themselves, insolubilization by the interaction thereof and the like reactions are also included in the nonspecific reactions in the *Limulus* assay, as long as they affect on the results of *Limulus* assay.

Means for Solving the Problems

With the aim of solving the aforementioned problems, the inventors of the present invention have conducted intensive studies and found as a result that nonspecific reactions in the *Limulus* assay can be effectively inhibited when a pretreatment is carried out by allowing an alkali metal sulfate and/or an alkaline earth metal sulfate to contact with a sample which is subjected to the *Limulus* assay under such a condition that its final concentration becomes 20 mM or more, or a pretreatment is carried out by allowing an alkali metal halide and/or an alkaline earth metal halide to contact with a sample which is subjected to a *Limulus* assay under such a condition that its final concentration becomes more than 0.4 M and equal to or lower than 1.2 M. Thus, the present invention is accomplished.

That is, the present invention provides a pretreatment agent for a sample to be subjected to a *Limulus* assay, comprising an alkali metal sulfate and/or an alkaline earth metal sulfate, wherein the pretreatment agent is allowed to contact with the sample under such conditions that the sulfate has a final concentration of 20 mM or more, or an alkali metal halide and/or an alkaline earth metal halide, wherein the pretreatment agent is allowed to contact with the sample under such conditions that the halide has a final concentration of from more than 0.4 M to 1.2 M or less (to be referred to as "pretreatment agent of the present invention" hereinafter). It is preferable that the alkali metal is one or two or more of alkali metals selected from the group consisting of lithium, sodium and potassium. Additionally, it is preferable that the alkaline earth metal is magnesium and/or calcium. Additionally, it is preferable that final concentration of the sulfate is from 20 mM to 500 mM. It is preferable that the halide is fluoride and/or chloride. Additionally, it is preferable that the object of the *Limulus* assay is BG. Additionally, it is preferable that the aforementioned sample is a sample derived from a living body. It is preferable that the sample derived from a living body is a body fluid or a substance derived therefrom. It is preferable that the body fluid is blood. It is desirable that this blood is one or more of blood selected from the group consisting of a blood derived from an animal of hyper globulinemia, a hemolysis-caused blood, a blood derived from an animal of hyperbilirubinemia and a blood derived from an animal of hyper chylomicronemia.

Additionally, the present invention also provides a *Limulus* reagent kit (to be referred as "a kit of the present invention") which comprises the pretreatment agent of the present invention as a composing article, a method for pre-treating a sample, which comprises pretreatment of a sample to be subjected to the *Limulus* assay with an alkali metal sulfate and/or an alkaline earth metal sulfate having a final concentration of 20 mM or more, or pretreatment with an alkali metal halide and/or an alkaline earth metal halide having a final concentration of from more than 0.4 M to 1.2 M or less (to be referred to as "pretreatment method of the present invention" hereinafter), and a *Limulus* assay method, which comprises the step of pre-treating a sample to be subjected to the *Limulus* assay with an alkali metal sulfate and/or an alkaline earth metal sulfate having a final concentration of 20 mM or more, or comprises the step of pre-treating it with an alkali metal halide and/or an alkaline earth metal halide having a final concentration of more than 0.4 M and equal to or lower than 1.2 M (to be referred to as "assay method of the present invention" hereinafter).

EFFECT OF THE INVENTION

The pretreatment agent of the present invention is markedly useful, since nonspecific reactions in the *Limulus* reaction can be inhibited conveniently, quickly, inexpensively and effectively and accuracy of the *Limulus* assay can be further improved, when a sample to be subjected to the *Limulus* assay is pre-treated by using it. Also, the kit of the present invention is markedly useful, since the *Limulus* assay having further high accuracy due to inhibition of nonspecific reactions can be quickly carried out by using it. Additionally, the pretreatment method of the present invention and assay method of the present invention are also markedly useful, since nonspecific reactions in the *Limulus* assay can be effectively inhibited and the *Limulus* assay having further high accuracy can be carried out conveniently, quickly and inexpensively.

BEST MODE FOR CARRYING OUT THE INVENTION

The following describes the present invention in detail based on the best mode for carrying out the present invention.

<1> Pretreatment Agent of the Present Invention

The pretreatment agent of the present invention is a pretreatment agent for a sample to be subjected to a *Limulus* assay, comprising an alkali metal sulfate and/or an alkaline earth metal sulfate, and is allowed to contact with the sample under such conditions that the sulfate has a final concentration of 20 mM or more (to be referred also to as "first pretreatment agent of the present invention" hereinafter), and a pretreatment agent for a sample to be subjected to a *Limulus* assay, comprising an alkali metal halide and/or an alkaline earth metal halide wherein the pretreatment agent is allowed to contact with the sample under such conditions that the halide(s) has a final concentration of from more than 0.4 M to 1.2 M or less (to be referred also to as "second pretreatment agent of the present invention" hereinafter). Additionally, in the following, the "pretreatment agent of the present invention" should include both of the "first pretreatment agent of the present invention" and the "second pretreatment agent of the present invention". Although the "alkali metal" as used herein is not particularly limited, as long as it is a metal recognized as an alkali metal in the technical field of the invention, one or two or more alkali metal(s) selected from the group consisting of lithium, sodium and potassium is preferable.

Additionally, although the "alkaline earth metal" as used herein is also not particularly limited, as long as it is a metal recognized as an alkaline earth metal in the technical field of the present invention, but magnesium and/or calcium is preferable.

Additionally, the "halide" as used herein is not particularly limited too, with the proviso that it is a substance recognized as a halide in said technical field, but it is particularly desirably fluoride and/or chloride.

The first pretreatment agent of the present invention should contain at least one species of such alkali metal sulfates and alkaline earth metal sulfates. Accordingly, the first pretreatment agent of the present invention may contain, for example, "sodium sulfate" alone as the alkali metal sulfate and alkaline earth metal sulfate, or may further contain one species or more of other sulfates (for example, lithium sulfate, potassium sulfate, magnesium sulfate, calcium sulfate and the like).

Additionally, although final concentration of the alkali metal sulfate and/or alkaline earth metal sulfate when the sulfate is allowed to contact with a sample to be subjected to the *Limulus* assay is not particularly limited, as long as it is 20 mM or more, it is preferably from 20 mM to 500 mM, more preferably from 30 mM to 450 mM, further preferably from 35 mM to 450 mM, and particularly preferably from 35 mM to 400 mM.

In this connection, when two species or more of the alkali metal sulfate and alkaline earthy metal sulfate are contained in the first pretreatment agent of the present invention, this "final concentration" means final concentration as the total of these sulfates.

The second pretreatment agent of the present invention may contain at least one species of such alkali metal halides and alkaline earth metal halides. Accordingly, the second pretreatment agent of the present invention may contain, for example, "potassium chloride" alone as the alkali metal halide and alkaline earth metal halide, or may further contain one species or more of other alkali metal halides and alkaline earth metal halides (e.g., lithium chloride, sodium chloride, magnesium chloride, calcium chloride, lithium fluoride, sodium fluoride, potassium fluoride, magnesium fluoride, calcium fluoride and the like).

Additionally, although final concentration of the alkali metal halide and/or alkaline earth metal halide when the halide is allowed to contact with a sample to be subjected to the *Limulus* assay is not particularly limited, as long as it is from more than 0.4 M to 1.2 M or less, it is preferably from more than 0.4 M to 1.0 M or less, more preferably from more than 0.4 M to 0.8 M or less, further preferably from 0.5 M to 0.8 M, and particularly preferably from 0.5 M to 0.7 M.

In this connection, when two species or more of the alkali metal halide and alkaline earthy metal halide are contained in the second pretreatment agent of the present invention, the "final concentration" means final concentration as the total of these halides.

Additionally, although the "sample to be subjected to the *Limulus* assay" which becomes the object of the contact of the pretreatment agent of the present invention is not particularly limited as long as it is a sample to be subjected to the *Limulus* assay, a sample which is subjected to the *Limulus* assay for the measurement of BG or endotoxin is preferable, and a sample which is subjected to the *Limulus* assay for the measurement of BG is more preferable.

Additionally, kind of the sample also is not particularly limited as long as it is a sample derived from the living body.

Although the "sample derived from the living body" is not particularly limited as long as it is collected from the living body of a animal including human, a body fluid or a material derived therefrom is preferable.

Although the "body fluid" is not particularly limited as long as it is a liquid which is present in the living body of an animal including human, blood is preferable.

When the "blood" is selected as the body fluid, the origin and the like of the blood are not particularly limited, and blood of every animal (including human) under every situation can be used. Particularly, it is preferable that the blood is one or more of blood selected from the group consisting of a blood derived from an animal of hyper globulinemia, a hemolysis-caused blood, a blood derived from an animal of hyperbilirubinemia and a blood derived from an animal of hyper chylomicronemia. Among these bloods, a human-derived blood is most preferable.

Additionally, the "material derived from a body fluid" means that it is not a body fluid itself which is present in the living body but a material obtained from a body fluid by a certain treatment. Accordingly, various types of the "material derived from a body fluid" can be used based on the kind and the like of each body fluid. For example, when the body fluid is a "blood", the blood includes blood plasma, sera and the like as an example of the material derived therefrom, and any one of them can be used as the sample to be subjected to the *Limulus* assay (subject of the treatment by the pretreatment agent of the present invention).

The method for the pretreatment of a sample using the first pretreatment agent of the present invention is not particularly limited as long as the alkali metal sulfate and/or alkaline earth metal sulfate contained in the first pretreatment agent of the present invention is maintained at a final concentration of 20 mM or more under a situation wherein it is contacted with the sample to be subjected to the *Limulus* assay. The method for allowing both of them to contact with each other is not particularly limited too, as long as the alkali metal sulfate and/or alkaline earth metal sulfate contained in the first pretreatment agent of the present invention is finally maintained under such a condition. For example, the first pretreatment agent of the present invention may be added to the sample; the sample may be added to the first pretreatment agent of the present invention; or both of them may be added at the same time.

The method for the pretreatment of a sample using the second pretreatment agent of the present invention is not particularly limited as long as the alkali metal halide and/or alkaline earth metal halide contained in the second pretreatment agent of the present invention is maintained at a final concentration of from more than 0.4 M to 1.2 M or less under a situation wherein it is contacted with the sample to be subjected to the *Limulus* assay. The method for allowing both of them to contact with each other is also not particularly limited, as long as the alkali metal halide and/or alkaline earth metal halide contained in the second pretreatment agent of the present invention is finally maintained under such conditions. For example, the second pretreatment agent of the present invention may be added to the sample; the sample may be added to the second pretreatment agent of the present invention; or both of them may be added at the same time.

Additionally, although the time, temperature and the like for allowing the pretreatment agent of the present invention to contact with a sample are not particularly limited as long as nonspecific *Limulus* reaction can be reduced to the desired degree by the pretreatment agent of the present invention, and can be optionally set by those skilled in the art. For example, when blood plasma is used as the sample, they may be for example, from about 30° C. to 75° C. for about from 5 minutes to 2 hours, preferably at about from 30° C. to 50° C. for about from 5 minutes to 1 hour, more preferably at about from 30° C. to 45° C. for about from 5 minutes to 30 minutes, particularly preferably at about from 35° C. to 40° C. for about from 5 minutes to 20 minutes. However, they are not limited thereto.

In this connection, the alkali metal sulfate and/or alkaline earth metal sulfate content and the like in the first pretreatment agent of the present invention are also not particularly limited, as long as the first pretreatment agent of the present invention comprises the alkali metal sulfate and/or alkaline earth metal sulfate wherein the pretreatment agent is allowed to contact with a sample under such conditions that the sulfate has a final concentration of 20 mM or more. Final concentration of the alkali metal sulfate and/or alkaline earth metal sulfate when the sulfate is allowed to contact with the sample is not also particularly limited, as long as it is 20 mM or more as described above, and it is for example from 20 mM to 500 mM, particularly from 30 mM to 450 mM, particularly from 35 mM to 450 mM, particularly from 35 mM to 400 mM and the like.

Also, the alkali metal halide and/or alkaline earth metal halide content and the like in the second pretreatment agent of the present invention are not particularly limited too as long as the second pretreatment agent of the present invention comprises the alkali metal halide and/or alkaline earth metal halide and is allowed to contact with a sample under such conditions that halide has a final concentration of from more than 0.4 M to 1.2 M or less. Final concentration of the alkali metal halide and/or alkaline earth metal halide when it is allowed to contact with the sample is also not particularly limited as long as it is from more than 0.4 M to 1.2 M or less as described above, and it is for example, from more than 0.4 M and to 1.0 M or less, particularly from more than 0.4 M to 0.8 M or less, particularly from 0.5 M to 0.8 M, particularly from 0.5 M to 0.7 M and the like.

Also, the first pretreatment agent of the present invention may contain other component as long as it contains at least an alkali metal sulfate and/or alkaline earth metal sulfate. Such other components include as an example, a component which inhibits nonspecific *Limulus* reaction (an alkali metal hydroxide and/or alkaline earth metal hydroxide, an alkali metal halide and/or alkaline earth metal halide or the like. Please see Examples), a component which is acceptable as a reagent or diagnostic agent among various additive agents and the like.

Additionally, the second pretreatment agent of the present invention may further contain other components as long as it contains at least an alkali metal halide and/or alkaline earth metal halide. Such other components includes for example, a component which inhibits nonspecific *Limulus* reaction (an alkali metal hydroxide and/or alkaline earth metal hydroxide, an alkali metal sulfate and/or alkaline earth metal sulfate or the like. Please see Examples), a component which is acceptable as a reagent or diagnostic agent among various additive agents and the like.

The aforementioned additive agents includes a stabilizing agent, an emulsifying agent, an osmotic pressure adjusting agent, a buffer agent, a tonicity agent, a preservative, a pH adjusting agent, a coloring agent, an excipient, a binder, a lubricant, a disintegrator and the like can be exemplified.

When an alkali metal hydroxide and/or alkaline earth metal hydroxide is further contained as a component of the pretreatment agent of the present invention, it is preferable to set its final concentration to be from 0.03 M to 0.07 M, particularly from 0.03 M to 0.06 M, as its final concentration when it is allowed to contact with a sample. Also, when an alkali metal halide and/or alkaline earth metal halide is further contained as a component of the first pretreatment agent of the present invention, it is preferable to set its final concentration to be from more than 0.4 M to 1.2 M or less, particularly from more than 0.4 M to 1.0 M or less, particularly from more than 0.4 M to 0.8 M or less, particularly from 0.5 M to 0.8 M, particularly from 0.5 M to 0.7 M, when it is allowed to contact with a sample. Additionally, when an alkali metal sulfate and/or alkaline earth metal sulfate is further contained as a component of the second pretreatment agent of the present invention, it is preferable to set its final concentration to be 20 mM or more, particularly from 20 mM to 500 mM, particularly from 30 mM to 450 mM, particularly from 35 mM to 450 mM, particularly from 35 mM to 400 mM, when it is allowed to contact with a sample.

Particularly from the viewpoint of more effectively inhibiting nonspecific *Limulus* reaction, it is more preferable that an alkali metal sulfate and/or alkaline earth metal sulfate, an alkali metal hydroxide and/or alkaline earth metal hydroxide and an alkali metal halide and/or alkaline earth metal halide is contained in the pretreatment agent of the present invention. In that case, final concentration of each component when the agent is allowed to contact with a sample is also not particularly limited. As an example, all combinations of final concentrations described as examples can also be demonstrated.

Namely, for example, the final concentration of an alkali metal sulfate and/or alkaline earth metal sulfate, when the first pretreatment agent of the present invention is contact with a sample, can be set to be 20 mM or more, and the final concentration of an alkali metal hydroxide and/or alkaline earth metal hydroxide can be set to be from 0.03 M to 0.07 M, particularly from 0.03 M to 0.06 M in the same manner, and the final concentration of an alkali metal halide and/or alkaline earth metal halide can be set to be from more than 0.4 M and equal to or lower than 1.2 M, particularly more than 0.4 M to 1.0 M or less, particularly from more than 0.4 M to 0.8 M or less, particularly from 0.5 M to 0.8 M, particularly from 0.5 M to 0.7 M, in the same manner.

In the same manner, also in a case where the final concentration of an alkali metal sulfate and/or alkaline earth metal sulfate is set to be from 20 mM to 500 mM when the first pretreatment agent of the present invention is allowed to contact with a sample, the final concentration of an alkali metal hydroxide and/or alkaline earth metal hydroxide can be set to be from 0.03 M to 0.07 M, particularly from 0.03 M to 0.06 M similarly, and the final concentration of an alkali metal halide and/or alkaline earth metal halide can be set to be more than 0.4 M to 1.2 M or less, particularly from more than 0.4 M to 1.0 M or less, particularly from more than 0.4 M to 0.8 M or less, particularly from 0.5 M to 0.8 M, particularly from 0.5 M to 0.7 M, similarly.

In the same manner, also in a case where the final concentration of an alkali metal sulfate and/or alkaline earth metal sulfate is set to be from 30 mM to 450 mM when the first pretreatment agent of the present invention is allowed to contact with a sample, the final concentration of an alkali metal hydroxide and/or alkaline earth metal hydroxide can be set to be from 0.03 M to 0.07 M, particularly from 0.03 M to 0.06 M similarly, and the final concentration of an alkali metal halide and/or alkaline earth metal halide can be set to be from more than 0.4 M to 1.2 M or less, particularly from more than 0.4 M to 1.0 M or less, particularly from more than 0.4 M to 0.8 M or less, particularly from 0.5 M to 0.8 M, particularly from 0.5 M to 0.7 M, similarly.

In the same manner, also in a case where the final concentration of an alkali metal sulfate and/or alkaline earth metal sulfate is set to be from 35 mM to 450 mM when the first pretreatment agent of the present invention is allowed to contact with a sample, the final concentration of an alkali metal hydroxide and/or alkaline earth metal hydroxide can be set to be from 0.03 M to 0.07 M, particularly from 0.03 M to 0.06 M similarly, and the final concentration of an alkali metal halide and/or alkaline earth metal halide can be set to be from 0.4 M to 1.2 M or less, particularly from more than 0.4 M to 1.0 M or less, particularly from more than 0.4 M to 0.8 M or less, particularly from 0.5 M to 0.8 M, particularly from 0.5 M to 0.7 M, similarly.

In the same manner, also in a case where the final concentration of an alkali metal sulfate and/or alkaline earth metal sulfate is set to be from 35 mM to 400 mM when the first pretreatment agent of the present invention is allowed to contact with a sample, the final concentration of an alkali metal hydroxide and/or alkaline earth metal hydroxide can be set to be from 0.03 M to 0.07 M, particularly from 0.03 M to 0.06 M similarly, and the final concentration of an alkali metal halide and/or alkaline earth metal halide to be from more than 0.4 M to or lower than 1.2 M or less, particularly from more than 0.4 M to 1.0 M or less, particularly from more than 0.4 M to 0.8 M or less, particularly from 0.5 M to 0.8 M, particularly from 0.5 M to 0.7 M, similarly.

Additionally, for example, when the second pretreatment agent of the present invention is allowed to contact with a sample, the final concentration of an alkali metal halide and/or alkaline earth metal halide can be set to be from more than 0.4 M to 1.2 M or less, and the final concentration of an alkali metal hydroxide and/or alkaline earth metal hydroxide can be set to be from 0.03 M to 0.07 M, particularly from 0.03 M to 0.06 M similarly, and the final concentration of an alkali metal sulfate and/or alkaline earth metal sulfate can be set to be 20 mM or more, particularly from 20 mM to 500 mM, particularly from 30 mM to 450 mM, particularly from 35 mM to 450 mM, particularly from 35 mM to 400 mM, similarly.

In the same manner, also in a case where when the final concentration of an alkali metal halide and/or alkaline earth metal halide is set to be from more than 0.4 M to 1.0 M or less when the second pretreatment agent of the present invention is allowed to contact with a sample, the final concentration of an alkali metal hydroxide and/or alkaline earth metal hydroxide can be set to be from 0.03 M to 0.07 M, particularly from 0.03 M to 0.06 M similarly, and the final concentration of an alkali metal sulfate and/or alkaline earth metal sulfate can be set to be 20 mM or more, particularly from 20 mM to 500 mM, particularly from 30 mM to 450 mM, particularly from 35 mM to 450 mM, particularly from 35 mM to 400 mM, similarly.

In the same manner, also in a case where the final concentration of an alkali metal halide and/or alkaline earth metal halide is set to be from more than 0.4 M to 0.8 M or lower when the second pretreatment agent of the present invention is allowed to contact with a sample, the final concentration of an alkali metal hydroxide and/or alkaline earth metal hydroxide can be set to be from 0.03 M to 0.07 M, particularly from 0.03 M to 0.06 M similarly, and the final concentration of an alkali metal sulfate and/or alkaline earth metal sulfate can be set to be 20 mM or more, particularly from 20 mM to 500 mM, particularly from 30 mM to 450 mM, particularly from 35 mM to 450 mM, particularly from 35 mM to 400 mM, similarly.

In the same manner, also in a case where the final concentration of an alkali metal halide and/or alkaline earth metal halide is set to be from 0.5 M to 0.8 M when the second pretreatment agent of the present invention is allowed to contact with a sample, the final concentration of an alkali metal hydroxide and/or alkaline earth metal hydroxide can be set to be from 0.03 M to 0.07 M, particularly from 0.03 M to 0.06 M in the similarly, and the final concentration of an alkali metal sulfate and/or alkaline earth metal sulfate can be set to be 20 mM or more, particularly from 20 mM to 500 mM, particularly from 30 mM to 450 mM, particularly from 35 mM to 450 mM, particularly from 35 mM to 400 mM, similarly.

In the same manner, also in a case where the final concentration of an alkali metal halide and/or alkaline earth metal halide is set to be from 0.5 M to 0.7 M when the second pretreatment agent of the present invention is allowed to contact with a sample, the final concentration of an alkali metal hydroxide and/or alkaline earth metal hydroxide can be set to a level of from 0.03 M to 0.07 M, particularly from 0.03 M to 0.06 M similarly, and the final concentration of an alkali metal sulfate and/or alkaline earth metal sulfate to a level of 20 mM or more, particularly from 20 mM to 500 mM, particularly from 30 mM to 450 mM, particularly from 35 mM to 450 mM, particularly from 35 mM to 400 mM, similarly.

In this connection, although some of these substances may not be dissolved completely at the aforementioned concentrations according to the temperature, solvent, other solute and the like conditions, and in that case, the maximum concentration at which the substance can be dissolved may be used.

Additionally, dosage forms of the pretreatment agent of the present invention are also not particularly limited, as long as the final concentration of an alkali metal sulfate and/or alkaline earth metal sulfate contained in the first pretreatment agent of the present invention can be set to be a level of 20 mM or more when it contacts with a sample, or the final concentration of an alkali metal halide and/or alkaline earth metal halide contained in the second pretreatment agent of the present invention can be set to be from more than 0.4 M to 1.2 M or lower when it to contacts with a sample. For example, the pretreatment agent of the present invention may be made into preparations in the form of solutions containing an alkali metal sulfate and/or alkaline earth metal sulfate or alkali metal halide and/or alkaline earth metal halide, or into powders, granules and the like solid preparations which are dissolved when used. Additionally, for example, when it is provided as the preparations in the form of solutions, it may be provided in the frozen state or provided directly as the solutions.

The pretreatment agent of the present invention can be produced by a general method for producing a reagent, a diagnostic agent and the like, after making it into a preparation which has the characteristics described in the above.

By carrying out pretreatment of a sample to be subjected to a *Limulus* assay using such a pretreatment agent of the present invention, nonspecific reactions in the *Limulus* assay can be inhibited conveniently, quickly, inexpensively and effectively and accuracy of the *Limulus* assay can be further improved.

<2> Kit of the Present Invention

The kit of the present invention is a *Limulus* reagent kit which comprises the pretreatment agent of the present invention as a composing article. With regard to the pretreatment agent of the present invention, please see the aforementioned descriptions.

The kit of the present invention may contain other composing articles with as long as it contains at least the pretreatment agent of the present invention as a composing article. Although such other composing articles include for example, a *Limulus* reagent (a limuloid amoebocyte lysate), a coloring synthetic substrate, a mixture thereof, a buffer liquid, distilled water, standard substances (endotoxin, BG and the like), a microplate and the like, they are not particularly limited thereto.

The pretreatment agent of the present invention as a composing article of the kit of the present invention can be produced and used as described above. Additionally, with regard to the other composing articles of the kit of the present invention, they can be produced and used in accordance with the production methods, application methods and the like of the conventionally known *Limulus* reagents and related reagents thereof.

By using kit of the present invention, a *Limulus* assay having more higher accuracy wherein nonspecific reactions are inhibited can be carried out quickly.

<3> Pretreatment Method of the Present Invention

The pretreatment method of the present invention is a method for pretreatment of a sample, comprising that a sample to be subjected to the *Limulus* assay is pre-treated with an alkali metal sulfate and/or alkaline earth metal sulfate having a final concentration of 20 mM or more, or with an alkali metal halide and/or alkaline earth metal halide having a final concentration of from more than 0.4 M to 1.2 M or lower. All of the meanings and preferred ranges of the "a sample to be subjected to the *Limulus* assay", "a final concentration (20 mM or more)", "alkali metal sulfate and/or alkaline earth metal sulfate", "a final concentration (from more than 0.4 M to 1.2 M or lower)" "alkali metal halide and/or alkaline earth metal halide" "pretreatment" and the like terms as used herein, and other substances which are acceptable in carrying out the pretreatment, treatment and the like methods and the like are the same as the aforementioned descriptions on the pretreatment agent of the present invention.

<4> Assay Method of the Present Invention

The assay method of the present invention is a *Limulus* assay method, which comprises the step of pretreatment of a sample to be subjected to the *Limulus* assay with an alkali metal sulfate and/or alkaline earth metal sulfate having a final concentration of 20 mM or more, or the step of pretreatment of it with an alkali metal halide and/or alkaline earth metal halide having a final concentration of from more than 0.4 M to 1.2 M or lower. All of the meanings and preferred ranges of the "a sample to be subjected to the *Limulus* assay", "a final concentration (20 mM or more)", "alkali metal sulfate and/or alkaline earth metal sulfate", "a final concentration (more than 0.4 M and equal to or lower than 1.2 M)" "alkali metal halide and/or alkaline earth metal halide" "pretreatment" and the like terms as used herein, and other substances which are acceptable in carrying out the pretreatment, treatment and the like methods and the like are the same with the aforementioned descriptions on the pretreatment agent of the present invention.

Additionally, the assay method of the present invention may contain other steps and the like, as long as it is a *Limulus* assay method which comprises at least the step pretreatment of a sample to be subjected to the *Limulus* assay with an alkali metal sulfate and/or alkaline earth metal sulfate having a final concentration of 20 mM or more, or is a *Limulus* assay method which comprises at least the step for pretreatment of it with an alkali metal halide and/or alkaline earth metal halide having a final concentration of from more than 0.4 M to 1.2 M or lower. For example, it may contain a step for carrying out a certain processing prior to the pretreatment of a sample, a step for converting the data obtained by the *Limulus* assay into other data and other steps. Additionally, the *Limulus* assay can be carried out by conventionally known general methods, except for the point that a sample to be subjected to the *Limulus* assay is pre-treated with an alkali metal sulfate and/or alkaline earth metal sulfate having a final concentration of 20 mM or more, or a sample to be subjected to the *Limulus* assay is pre-treated with an alkali metal halide and/or alkaline earth metal halide having a final concentration of from more than 0.4 M to 1.2 M or lower.

By such pretreatment method of the present invention and assay method of the present invention, nonspecific reactions in the *Limulus* reaction can be effectively inhibited, and a *Limulus* assay having more higher accuracy can be carried out conveniently, quickly and inexpensively.

EXAMPLES

Although the following describes the present invention more specifically based on inventive Examples, the technical scope of the present invention is not limited thereto. The Examples are Examples in which sodium sulfate ($Na_2SO_4$)

was used as an example of the alkali metal sulfate and/or alkaline earth metal sulfate, or an alkali metal halide (KCl) in the pretreatment agent and BG was used as the object of the *Limulus* assay. Additionally, influence of the concentration of an alkali metal hydroxide (KOH) when it is contained in the pretreatment agent was also shown as a reference example.

(1) Materials, Methods and the Like (1-1) Preparation of Model Blood Plasma and Serum and Blood Plasma of Hemolysis-Caused Blood Model blood plasmas and the like as blood plasmas and the like of bloods under various conditions were prepared in the following manner. Additionally, preparation method of blood plasma of hemolysis-caused blood is also shown in the following.

Model blood plasma of hyper γ-globulinemia animal: Prepared by adding γ-globulin (Donated Blood Glovenin-I-Nichiyaku; manufactured by Nihon Pharmaceutical Co., Ltd.) to blood plasma collected from a healthy volunteer, to be a concentration of 6000 mg/dL.

Model blood plasma of hemolysis-caused blood: Prepared by adding hemoglobin (Hemoglobin, from Human; Wako Pure Chemical Industries) to blood plasma collected from a healthy volunteer.

Model blood plasma of hyperbilirubinemia animal: Prepared by adding bilirubin (Bilirubin; Wako Pure Chemical Industries) to blood plasma collected from a healthy volunteer.

Model blood plasma of hyper chylomicronemia animal: Prepared by adding a fat emulsion for intravenous injection use (trade name: Intralipid; Fresenius Kabi AB) to blood plasma collected from a healthy volunteer.

Additionally, various model sera were prepared in the same manner as described above, using a "serum" collected from a healthy volunteer.

Blood plasma of hemolysis-caused blood: Prepared by once freeze-thawing heparin blood collected from a healthy volunteer, centrifuging it and then collecting its supernatant.

(1-2) *Limulus* Assay

Solution to be tested (0.025 mL) was put into a BG-free microplate (Toxipet Plate 96F; Seikagaku Corporation), and 0.1 mL of a BG assay reagent (Fungitech (registered trademark) G Test MK main reaction reagent set; Seikagaku Corporation) was added thereto. It was incubated at 37° C. for 30 minutes using a microplate reader equipped with a thermostat function (Well Reader SK 603; Seikagaku Corporation), and then its absorbance at 405 nm (control wavelength: 492 nm) was measured to determine BG in the solution to be tested.

(1-3) Detection of Nonspecific Reactions

Nonspecific *Limulus* reactions which are not caused by BG were detected by the use of the BG assay reagent of the aforementioned (1-2) to which the formic acid hydrolyzate of curdlan prepared by the method described in WO 90/02951 or a factor G activation inhibitor derived from *Laminaria digitata* laminaran (these are called "GI" as a whole hereinafter) has been added to a final concentration of 10 μg/mL or more (BG assay reagent wherein induction of *Limulus* reaction was inhibited), and shown by a value converted to a standard BG (pachyman) concentration (to be referred simply to as "BG concentration" in Tables 1, 3, 4 and 9 which are shown later).

(1-4) Calculation of Addition Recovery Yield

BG was added to 0.1 mL of blood plasma collected from a healthy volunteer to be a predetermined final concentration, and it was used as a sample. Addition recovery yield of BG was calculated as a percentage of the amount of BG recovered from solution to be tested, when the amount of BG recovered from a control (water which contains a predetermined final concentration of BG) was defined as 100%.

(2) Results and the Like (2-1) Reference Example 1

The influence of concentration when an alkali metal hydroxide (KOH) was contained in a pretreatment agent was demonstrated. To 0.005 mL of the aforementioned model blood plasma (model blood plasma of hyper γ-globulinemia animal), 0.02 mL portion of a pretreatment agent was added. Composition of the pretreatment agent was set to be various concentrations (0.15 M, 0.1 M, 0.08 M, 0.07 M, 0.05 M or 0 M) of KOH, 0.3 M KCl, 20 mM EDTA and 0.1% polybrene. Thereafter, it was incubated at 37° C. for 10 minutes using a microplate reader equipped with a thermostat function (Well Reader SK 603; Seikagaku Corporation) and used as a solution to be tested. In this connection, final concentrations of each component of the pretreatment agent in the solution to be tested (a mixture of a sample and the pretreatment agent) were 0.12 M, 0.08 M, 0.064 M, 0.056 M, 0.04 M or 0 M of KOH, 0.24 M of KCl, 16 mM of EDTA and 0.08% of polybrene.

A *Limulus* assay was carried out on the solution to be tested. Additionally, the *Limulus* assay was carried out in the same manner on water and a 500 pg/mL BG aqueous solution as controls without the pretreatment. The results are shown in Table 1.

TABLE 1

| | | Measured value (mAbs/min) | | BG concentration (pg/mL) |
|---|---|---|---|---|
| | | | Mean value | |
| Standard | H₂O | 0.06 | 0.06 | |
| | | 0.06 | | |
| | | 0.05 | | |
| | 500 pg/mL BG | 24.11 | 23.66 | |
| | | 23.55 | | |
| | | 23.34 | | |
| Treatment with pretreatment agent | 0.12 M KOH | 1.08 | 0.96 | 19.2 |
| | | 0.71 | | |
| | | 1.10 | | |
| | 0.08 M KOH | 0.81 | 0.89 | 17.6 |
| | | 0.85 | | |
| | | 1.01 | | |
| | 0.064 M KOH | 0.78 | 0.72 | 14.1 |
| | | 0.70 | | |
| | | 0.69 | | |
| | 0.056 M KOH | 0.40 | 0.39 | 7.1 |
| | | 0.41 | | |
| | | 0.37 | | |
| | 0.04 M KOH | 0.21 | 0.21 | 3.3 |
| | | 0.24 | | |
| | | 0.19 | | |
| | 0 M KOH | 0.52 | 0.52 | 9.8 |
| | | 0.56 | | |
| | | 4.47 | | |

From Table 1, it was shown that nonspecific reactions when the model blood plasma was used greatly changes by a slight difference in the alkali metal hydroxide (KOH) concentration in the liquid to be tested. Although the nonspecific reactions were hardly inhibited when concentration of the alkali metal hydroxide (KOH) is too large or 0 M, they were markedly inhibited at a final concentration of around 0.04 M and 0.056 M. Based on the result, it was shown that nonspecific reactions when the model blood plasma was used as the sample of Limulus assay can be effectively inhibited, by carrying out the pretreatment wherein the alkali metal hydroxide contacts with the sample at a final concentration of from 0.03 M to 0.07 M, particularly from 0.03 M to 0.06 M.

Additionally, the addition recover yield when concentration of the alkali metal hydroxide (KOH) in the pretreatment agent was set to 0.15 M or 0.05 M (each final concentrations in the solution to be tested was 0.12 M or 0.04 M, respectively) was calculated. BG was added thereto to be a final concentration of 20 pg/mL. The results are shown in Table 2.

TABLE 2

| Pretreatment | H$_2$O | | | | Model blood plasma | | | | Addition recovery yield (%) |
| | BG − | | BG + | | BG − | | BG + | | |
| | mAbs/min | BG concentration (pg/mL) | mAbs/min | BG concentration (pg/mL) | mAbs/min | BG concentration (pg/mL) | mAbs/min | BG concentration (pg/mL) | |
| | | Mean | | Mean | | Mean | | Mean | |
|---|---|---|---|---|---|---|---|---|---|
| 0.12 M KOH | 0.09 0.09 0.08 | 0.09 | 0.67 0.67 0.62 | 0.65 | 20 | 0.51 0.51 0.51 | 0.51 | 14.9 | 1.05 1.04 1.03 | 1.04 | 33.6 | 93.5 |
| 0.04 M KOH | 0.09 0.09 0.08 | 0.09 | 0.67 0.67 0.62 | 0.65 | 20 | 0.35 0.37 0.37 | 0.36 | 9.8 | 0.96 0.95 0.99 | 0.97 | 31.1 | 106.5 |

As shown in Table 2, good recovery yield was obtained without influence on the addition recovery yield, even when the pretreatment was carried out by allowing the alkali metal hydroxide (KOH) to contact with the sample at a final concentration of 0.12 M or 0.04 M.

(2-2) Example 1

The influence of concentration when an alkali metal halide (KCl) was contained in a pretreatment agent was demonstrated. The assay was carried out in the same manner as in the aforementioned Reference Example 1, except that composition of the pretreatment agent was set to be 0.15 M KOH, various concentration (0.3 M, 0.6 M and 0.9 M) of KCl, 20 mM EDTA and 0.1% polybrene. In this connection, final concentration of each component of the pretreatment agent in a solution to be tested (a mixture of the sample and pretreatment agent) is 0.12 M of KOH, 0.24 M, 0.48 M or 0.72 M of KCl, 16 mM of EDTA and 0.08% of polybrene. The results are shown in Table 3.

TABLE 3

| | | Measured value (mAbs/min) | | BG concentration (pg/mL) |
| | | | Mean value | |
|---|---|---|---|---|
| Standard | H$_2$O | 0.06 0.06 0.05 | 0.06 | |
| | 500 pg/mL BG | 24.11 23.55 23.34 | 23.66 | |
| Pretreatment (0.12 M KOH) | 0.24 M KCl | 2.13 1.81 2.00 | 1.98 | 40.6 |
| | 0.48 M KCl | 1.37 1.29 1.33 | 1.33 | 26.9 |
| | 0.72 M KCl | 0.89 0.76 1.14 | 0.93 | 18.5 |

From Table 3, it was shown that nonspecific reactions when the model blood plasma was used greatly changes by a difference in the alkali metal halide (KCl) concentration in the liquid to be tested. The nonspecific reactions were markedly inhibited when concentration of the alkali metal halide (KCl) was high.

Additionally, the same assay with the aforementioned treatment was carried out except for setting concentration of the alkali metal hydroxide (KOH) in the pretreatment agent to be 0.05 M (0.04 M in final concentration in the solution to be tested), with The results were shown in Table 4.

TABLE 4

| | | Measured value (mAbs/min) | | BG concentration (pg/mL) |
| | | | Average value | |
|---|---|---|---|---|
| Standard | H$_2$O | 0.11 0.07 0.06 | 0.08 | |

TABLE 4-continued

|  |  | Measured value (mAbs/min) |  | BG concentration (pg/mL) |
|---|---|---|---|---|
|  |  |  | Average value |  |
|  | 500 pg/mL BG | 25.43 | 24.97 |  |
|  |  | 24.48 |  |  |
|  |  | 24.99 |  |  |
| Pretreatment (0.04 M KOH) | 0.24 M KCl | 0.25 | 0.21 | 2.7 |
|  |  | 0.17 |  |  |
|  |  | 0.22 |  |  |
|  | 0.48 M KCl | 0.15 | 0.14 | 1.1 |
|  |  | 0.14 |  |  |
|  |  | 0.12 |  |  |
|  | 0.72 M KCl | 0.17 | 0.18 | 2.0 |
|  |  | 0.21 |  |  |
|  |  | 0.15 |  |  |

Also from Table 4, it was shown that nonspecific reactions in the model blood plasma are markedly inhibited by the alkali metal halide (KCl).

On the other hand, when concentration of the alkali metal halide was too high, there was a bad influence on the *Limulus* reaction itself. Accordingly, it was suggested based on Table 3 and Table 4 that the nonspecific reactions in the case where the model blood plasma was used as the sample for *Limulus* assay can be effectively inhibited without exerting substantial bad influence on the *Limulus* reaction, when the pretreatment was carried out by allowing the alkali metal halide to contact with the sample at a final concentration of from more than 0.4 M to 1.2 M or less, particularly from more than 0.4 M to 1.0 M or less, particularly from more than 0.4 M to 0.8 M or less, particularly from 0.5 M to 0.8 M, particularly from 0.5 M to 0.7 M.

Additionally, the addition recover yield in the aforementioned treatment, in a case where concentration of the alkali metal hydroxide (KOH) in the pretreatment agent was set to be 0.05 M (final concentrations in the solution to be tested was 0.04 M), was calculated. BG was added thereto to be a final concentration of 20 pg/mL. The results are shown in Table 5.

TABLE 5

| Pretreatment | H$_2$O |  |  |  |  | Model blood plasma |  |  |  | Addition recovery yield (%) |
|---|---|---|---|---|---|---|---|---|---|---|
|  | − |  | + |  |  | − |  | + |  |  |
|  | BG | | | | | | | | | |
|  | mAbs/min | Mean | concentration (pg/mL) | mAbs/min | Mean | BG concentration (pg/mL) | mAbs/min | Mean | BG concentration (pg/mL) | mAbs/min | Mean | BG concentration (pg/mL) | |
| 0.12 M KOH + 0.24 M KCl | 0.05 | 0.05 | 0.0 | 0.94 | 0.89 | 20.0 | 0.41 | 0.39 | 8.61 | 1.25 1.21 | 1.23 | 28.13 | 97.6 |
|  | 0.05 |  |  | 0.90 |  |  | 0.43 |  |  | 1.22 |  |  |  |
|  | 0.05 |  |  | 0.82 |  |  |  |  |  |  |  |  |  |
| 0.04 M KOH  KCl 0.24 (M) | 0.05 | 0.05 | 0.0 | 0.94 | 0.89 | 20.00 | 0.26 0.25 0.25 | 0.25 | 4.86 | 1.10 1.11 1.11 | 1.11 | 25.26 | 102.0 |
|  | 0.05 |  |  | 0.90 |  |  |  |  |  |  |  |  |  |
|  | 0.05 |  |  | 0.82 |  |  |  |  |  |  |  |  |  |
|  | 0.48 | 0.05 | 0.05 | 0.0 | 0.94 | 0.89 | 20.00 | 0.18 0.19 0.20 | 0.19 | 3.35 | 0.97 0.97 1.01 | 0.98 | 22.31 | 94.8 |
|  |  | 0.05 |  |  | 0.90 |  |  |  |  |  |  |  |  |
|  |  | 0.05 |  |  | 0.82 |  |  |  |  |  |  |  |  |
|  | 0.72 | 0.05 | 0.05 | 0.0 | 0.94 | 0.89 | 20.00 | 0.18 0.20 0.19 | 0.19 | 3.35 | 0.88 0.89 0.92 | 0.90 | 20.24 | 84.5 |
|  |  | 0.05 |  |  | 0.90 |  |  |  |  |  |  |  |  |
|  |  | 0.05 |  |  | 0.82 |  |  |  |  |  |  |  |  |

As shown in Table 5, good recovery yield was obtained without significant influence on the addition recovery yield, even when the pretreatment was carried out by allowing the alkali metal halide (KCl) to contact with the sample after increasing the final concentration to be 0.72 M.

Additionally, the addition recover yield by the aforementioned treatment, in a case where concentration of the alkali metal halide (KCl) in the pretreatment agent was set to 0.6 M (final concentrations in the solution to be tested was 0.48 M), and concentration of the alkali metal hydroxide (KOH) was set to be 0.05 M, 0.04 M, 0.03 M, 0.02 M or 0 M (final concentrations in the solution to be tested was 0.04 M, 0.032 M, 0.024 M, 0.016 M and 0 M), was calculated. BG was added thereto to a final concentration of 100 pg/mL. The results are shown in Table 6.

400 mM of $Na_2SO_4$. The results are shown in Table 7. In this connection, Table 7 was shown by the absorbance (A404/492) at the time of the commencement of the *Limulus* reaction.

TABLE 7

| | | | Measured value (A405/492) | |
|---|---|---|---|---|
| | | | | Mean |
| Pretreatment | $Na_2SO_4$ final concentration (mM) | 0 | 0.252 0.247 0.243 | 0.247 |

TABLE 6

| | | | | H₂O | | | | Model blood plasma | | | | |
|---|---|---|---|---|---|---|---|---|---|---|---|---|
| | | | | | | | | BG | | | | |
| | | | | – | | | | | | | | |
| | | | | | BG concentration | | | + | | | – | + | Addition |
| | | | mAbs/min | | | mAbs/min | BG concentration | mAbs/min | BG concentration | mAbs/min | BG concentration | recovery yield |
| | | | | Mean | (pg/mL) | | Mean | (pg/mL) | | Mean | (pg/mL) | | Mean | (pg/mL) | (%) |
| 0.048 M KCl | KOH (M) | 0.04 | 0.07 0.07 0.08 | 0.07 | 0.0 | 4.46 4.42 4.26 | 4.38 | 100.0 | 0.42 0.41 0.42 | 0.42 | 8.0 | 4.90 5.02 5.09 | 5.01 | 114.6 | 106.7 |
| | | 0.032 | 0.07 0.07 0.08 | 0.07 | 0.0 | 4.46 4.42 4.26 | 4.38 | 100.0 | 0.34 0.35 0.42 | 0.37 | 6.9 | 4.57 4.54 4.71 | 4.61 | 105.4 | 98.5 |
| | | 0.024 | 0.07 0.07 0.08 | 0.07 | 0.0 | 4.46 4.42 4.26 | 4.38 | 100.0 | 0.29 0.28 0.29 | 0.29 | 5.0 | 3.67 3.64 3.53 | 3.61 | 82.3 | 77.3 |
| | | 0.016 | 0.07 0.07 0.08 | 0.07 | 0.0 | 4.46 4.42 4.26 | 4.38 | 100.0 | 0.51 0.39 0.46 | 0.46 | 8.9 | 2.07 2.08 2.07 | 2.07 | 46.5 | 37.6 |
| | | 0 | 0.07 0.07 0.08 | 0.07 | 0.0 | 4.46 4.42 4.26 | 4.38 | 100.0 | 0.43 0.46 0.45 | 0.45 | 8.7 | 1.42 1.39 1.38 | 1.40 | 30.7 | 22.0 |

As shown in Table 6, when final concentration of the alkali metal halide (KCl) was increased to be 0.48 M, good recovery yield was obtained without significant influence on the addition recovery yield, even when the pretreatment was carried out by allowing the alkali metal hydroxide (KOH) to contact with the sample after reducing the final concentration to be 0.032 M.

(2-3) Example 2

Test Using Model Blood Plasma

The influence of concentration when an alkali metal sulfate ($Na_2SO_4$) was contained in a pretreatment agent was demonstrated. The assay was carried out in the same manner with the aforementioned Reference Example 1, except that composition of the pretreatment agent was set to be 0.15 M KOH, 0.3 M KCl, 20 mM EDTA, 0.1% polybrene and various concentrations (0 mM, 50 mM, 100 mM, 200 mM, 400 mM or 500 mM) of $Na_2SO_4$. In this connection, final concentration of each component of the pretreatment agent in solution to be tested (a mixture of the sample and pretreatment agent) are 0.12 M of KOH, 0.24 M of KCl, 16 mM of EDTA, 0.08% of polybrene and 0 mM, 40 mM, 80 mM, 160 mM, 320 mM or TABLE 7-continued

| | Measured value (A405/492) | |
|---|---|---|
| | | Mean |
| 40 | 0.157 0.173 0.211 | 0.180 |
| 80 | 0.105 0.111 0.102 | 0.106 |
| 160 | 0.068 0.074 0.076 | 0.073 |
| 320 | 0.063 0.064 0.061 | 0.063 |
| 400 | 0.062 0.062 0.062 | 0.062 |

It was shown in Table 7 that the nonspecific reactions in a case where the model blood plasma was used are inhibited by the alkali metal sulfate ($Na_2SO_4$) in the liquid to be tested.

The nonspecific reactions were inhibited according to the concentration of the alkali metal sulfate ($Na_2SO_4$), which reached almost plateau at a final concentration of 160 mM. It was suggested based on Table 7 that the nonspecific reactions in the case where the model blood plasma was used as the sample for *Limulus* assay can be effectively inhibited without exerting substantial bad influence upon the *Limulus* reaction, when the pretreatment is carried out by allowing the alkali metal sulfate to contact with the sample at a final concentration of 20 mM or more, particularly from 20 mM to 500 mM, particularly from 30 mM to 450 mM, particularly from 35 mM to 450 mM, and particularly preferably from 35 mM to 400 mM.

Additionally, the addition recover yield in the aforementioned treatment in case where concentration of the alkali metal hydroxide (KOH) in the pretreatment agent was set to be 0.05 M (final concentrations in the solution to be tested was 0.04 M), and concentration of the alkali metal halide (KCl) was set to be 0.6 M (final concentration in the solution to be tested was 0.48 M), was calculated. BG was added thereto to be a final concentration of 20 pg/mL. The results are shown in Table 8.

with each pretreatment agent having the following compositions.

Pretreatment agent 1: 0.15 M KOH, 0.3 M KCl, 20 mM EDTA and 0.1% polybrene (final concentrations of each component in the solution to be tested (a mixture of the sample and pretreatment agent): 0.12 M KOH, 0.24 M KCl, 16 mM EDTA and 0.08% polybrene)

Pretreatment agent 2: 0.05 M KOH, 0.3 M KCl, 20 mM EDTA and 0.1% polybrene (final concentrations of each component in the solution to be tested (a mixture of the sample and pretreatment agent): 0.04 M KOH, 0.24 M KCl, 16 mM EDTA and 0.08% polybrene)

Pretreatment agent 3: 0.05 M KOH, 0.6 M KCl, 20 mM EDTA and 0.1% polybrene (final concentrations of each component in the solution to be tested (a mixture of the sample and pretreatment agent): 0.04 M KOH, 0.48 M KCl, 16 mM EDTA and 0.08% polybrene)

Pretreatment agent 4: 0.05 M KOH, 0.6 M KCl, 20 mM EDTA, 0.1% polybrene and 50 mM $Na_2SO_4$ (final concentrations of each component in the solution to be

TABLE 8

| | | $H_2O$ | | | | Model blood plasma | | | | |
|---|---|---|---|---|---|---|---|---|---|---|
| | | BG | | | | | | | | |
| | | − | | + | | − | | + | | |
| | | mAbs/min | BG concentration | mAbs/min | BG concentration | mAbs/min | BG concentration | mAbs/min | BG concentration | Addition recovery yield |
| | | | Mean (pg/mL) | | Mean (pg/mL) | | Mean (pg/mL) | | Mean (pg/mL) | (%) |
| 0.12 M KOH + 0.24 M KCl | | 0.083 0.102 0.083 | 0.09 0.0 | 0.911 0.956 0.955 | 0.94 20.0 | 0.365 0.488 0.436 | 0.43 8.0 | 1.128 1.180 1.226 | 1.18 25.6 | 88.0 |
| 0.04 M KOH + 0.48 M KCl | $Na_2SO_4$ (mM) 0 | 0.083 0.102 0.083 | 0.09 0.0 | 0.911 0.956 0.955 | 0.94 20.0 | 0.189 0.165 0.186 | 0.18 2.1 | 0.966 0.941 0.943 | 0.95 20.2 | 90.5 |
| | 40 | 0.083 0.102 0.083 | 0.09 0.0 | 0.911 0.956 0.955 | 0.94 20.0 | 0.185 0.207 0.207 | 0.20 2.6 | 1.005 1.012 0.993 | 1.00 21.5 | 94.5 |
| | 80 | 0.083 0.102 0.083 | 0.09 0.0 | 0.911 0.956 0.955 | 0.94 20.0 | 0.198 0.172 0.181 | 0.18 2.2 | 0.960 0.980 0.982 | 0.97 20.8 | 92.9 |
| | 160 | 0.083 0.102 0.083 | 0.09 0.0 | 0.911 0.956 0.955 | 0.94 20.0 | 0.216 0.166 0.162 | 0.18 2.2 | 1.019 0.964 0.920 | 0.97 20.6 | 92.4 |
| | 320 | 0.083 0.102 0.083 | 0.09 0.0 | 0.911 0.956 0.955 | 0.94 20.0 | 0.186 0.178 0.170 | 0.18 2.1 | 0.928 0.917 0.832 | 0.89 18.9 | 83.9 |

From Table 8, even when the pretreatment was carried out by increasing final concentration of the alkali metal sulfate ($Na_2SO_4$) and allowing it to contact with the sample, good recovery yield was obtained without significant influence on the addition recovery yield at least up to a final concentration of 320 mM.

(2-4) Example 3

Test Using Clinical Samples

The assay was carried out in the same manner with the aforementioned Reference Example 1 except for using clinical samples (24 samples) which strongly show nonspecific reactions in the aforementioned treatment, and the treatment tested (a mixture of the sample and pretreatment agent): 0.04 M KOH, 0.48 M KCl, 16 mM EDTA, 0.08% polybrene and 40 mM $Na_2SO_4$)

Pretreatment agent 5: 0.05 M KOH, 0.6 M KCl, 20 mM EDTA, 0.1% polybrene and 200 mM $Na_2SO_4$ (final concentrations of each component in the solution to be tested (a mixture of the sample and pretreatment agent): 0.04 M KOH, 0.48 M KCl, 16 mM EDTA, 0.08% polybrene and 160 mM $Na_2SO_4$)

The results are shown in Table 9. In this connection, the term "denial" in Table 9 means that the patient from which the sample was derived was diagnosed as non-mycosis by the doctor, and the "doubt" means a case which was diagnosed as dubious of mycosis. Additionally, the term "CA" in Table 9 means *Candida* infection, and "MM" multiple myeloma, "LC" lung cancer, "CD" collagen disease, "FH" fulminant hepatitis, "MDS" myelodysplastic syndrome, and "ITP" sudden thrombocytopenic purpura, respectively.

TABLE 9

| Sample No. | Diagnosed Diagnosis | Name of Mycosis | Basal disease | BG concentration (ng/mL) Pretreatment agent 1 | Pretreatment agent 2 | Pretreatment agent 3 | Pretreatment agent 4 | Pretreatment agent 5 |
|---|---|---|---|---|---|---|---|---|
| 135 | Denial | — | MM | 62.3 | <3.9 (0.4) | <3.9 (3.2) | <3.9 (1.9) | <3.9 (1.9) |
| 56 | Denial | — | MM | 44.5 | <3.9 (2.1) | 4.8 | <3.9 (2.6) | <3.9 (3.0) |
| 383 | Denial | — | MM | 35.2 | 18.9 | 10.3 | <3.9 (3.8) | 4.9 |
| 215 | Denial | — | LC | 30.5 | 16.7 | 21.8 | 13.4 | 16 |
| 519 | Denial | — | MM | 47.1 | 18.8 | 8.6 | <3.9 (2.6) | <3.9 (2.9) |
| 485 | Denial | — | MM | 44.1 | 12.3 | 6.4 | <3.9 (1.8) | <3.9 (2.9) |
| 121 | Denial | — | CD | 33.6 | 13.5 | 12.1 | 4 | 5.2 |
| 293 | Denial | — | MM | 28.9 | 7.7 | <3.9 (2.6) | <3.9 (1.7) | <3.9 (1.9) |
| 474 | Doubt | CA | FH | 28.2 | 11.4 | <3.9 (3.7) | 6 | <3.9 (3.4) |
| 443 | Doubt | CA | FH | 23.9 | <3.9 (3.4) | 3.9 | 5.1 | <3.9 (2.1) |
| 89 | Denial | — | MM | 22.7 | <3.9 (3.8) | <3.9 (1.1) | <3.9 (2.7) | <3.9 (2.3) |
| 245 | Denial | — | MDS | 22.2 | 6.4 | <3.9 (2.8) | 5.7 | <3.9 (2.9) |
| 125 | Denial | — | MM | 21.9 | 6.3 | <3.9 (3.8) | <3.9 (3.3) | <3.9 (3.3) |
| 48 | Denial | — | MM | 21 | <3.9 (1.9) | <3.9 (2.8) | <3.9 (3.1) | <3.9 (2.2) |
| 332 | Denial | — | MM | 20.7 | 5.4 | <3.9 (3.0) | 4.6 | <3.9 (3.1) |
| 186 | Denial | — | MM | 20.2 | <3.9 (1.9) | <3.9 (3.3) | 4.9 | <3.9 (2.5) |
| 562 | Doubt | CA | FH | 18.9 | 9.5 | 4.5 | 6.5 | <3.9 (3.4) |
| 188 | Doubt | CA | FH | 17.7 | 7 | 6.6 | 7.7 | 6.1 |
| 523 | Doubt | CA | FH | 17.6 | 13.2 | 5.1 | 4.6 | <3.9 (3.2) |
| 437 | Denial | — | MM | 16.8 | <3.9 (2.0) | <3.9 (2.7) | 5 | <3.9 (2.9) |
| 142 | Denial | — | ITP | 16.3 | 4.7 | <3.9 (3.0) | 5 | <3.9 (3.2) |
| 172 | Denial | — | MM | 16.3 | <3.9 (2.2) | <3.9 (2.5) | <3.9 (3.6) | <3.9 (2.5) |
| 286 | Doubt | CA | FH | 15.5 | 8.1 | 5 | 6.7 | 3.9 |
| 233 | Doubt | CA | FH | 14.1 | <3.9 (3.7) | <3.9 (3.4) | 5.1 | 4.8 |

As shown in Table 9, high nonspecific reactions were detected when treated with a pretreatment agent (pretreatment agent 1) which has high alkali metal hydroxide (KOH) concentration and low alkali metal halide (KCl) concentration and does not contain alkali metal sulfate ($Na_2SO_4$). On the other hand, it was shown that the nonspecific reactions are markedly reduced when the alkali metal hydroxide (KOH) concentration was reduced (pretreatment agent 2), the alkali metal halide (KCl) concentration was further increased (pretreatment agent 3) and the alkali metal sulfate ($Na_2SO_4$) was further added (pretreatment agents 4 and 5).

(2-5) Example 4

Test Using Various Blood Plasmas and Sera

The assay was carried out in the same manner with the aforementioned Reference Example 1, except that a model blood plasma or model serum of a hyper globulinemia animal, a model blood plasma or model serum of a hemolysis-caused blood, a model blood plasma or model serum of a hyperbilirubinemia animal, a model blood plasma or model serum of a hyper chylomicronemia animal, or blood plasma of a hemolysis-caused blood were used as the sample in the aforementioned treatment and treated with the aforementioned pretreatment agent 1 or pretreatment agent 4.

As a result, in the case where use of any one of these samples were used, nonspecific reactions were markedly reduced when the pretreatment agent 4 (a composition to be included in the present invention) was used, in comparison with the pretreatment agent 1.

Based on the above results, it was shown that the nonspecific Limulus reactions in the case where the aforementioned model blood plasmas or bloods of the aforementioned disease animals were used as a sample can be effectively inhibited, by any one of the pretreatment in which an alkali metal hydroxide and/or alkaline earth metal hydroxide is allowed to contact with a sample at a final concentration of from 0.03 M to 0.07 M, particularly from 0.03 M to 0.06 M; the pretreatment in which an alkali metal halide and/or alkaline earth metal halide is allowed to contact with a sample at a final concentration of from more than 0.4 M to 1.2 M or lower, particularly from more than 0.4 M to 1.0 M or lower, particularly from more than 0.4 M to 0.8 M or lower, particularly from 0.5 M to 0.8 M, particularly from 0.5 M to 0.7 M; and the pretreatment in which an alkali metal sulfate and/or alkaline earth metal sulfate is allowed to contact with a sample at a final concentration of 20 mM or more, particularly from 20 mM to 500 mM, particularly from 30 mM to 450 mM, particularly from 35 mM to 450 mM, particularly from 35 mM to 400 mM. Additionally, it was shown that the nonspecific Limulus reactions can be inhibited more effectively by simultaneously carrying out these three treatments.

While the present invention has been described in detail and with reference to specific embodiments thereof, it will be apparent to one skilled in the art that various changes and modifications can be made therein without departing from the scope thereof.

This application is based on Japanese patent application No. 2005-20444 filed on Jan. 27, 2005 and Japanese patent application No. 2005-20445 filed on Jan. 27, 2005 and the entire contents thereof being hereby incorporated by reference. Further, all references cited herein are incorporated in their entireties.

INDUSTRIAL APPLICABILITY

All of the pretreatment agent of the present invention, the kit of the present invention, the pretreatment method of the present invention and the measurement method of the present invention can be used for the measurement of endotoxin and BG by Limulus reagent.

The invention claimed is:

1. A method for *Limulus* assay of a sample, which comprises
    pre-treating the sample with a pretreatment agent that comprises an alkali metal sulfate or an alkaline earth metal sulfat, or a combination thereof, at a final concentration of 20 mM to 500 mM; and
    subjecting the pretreated sample to *Limulus* assay.

2. The method according to claim 1, wherein the pretreatment agent further comprises an alkali metal halide or an alkaline earth metal halide, or a combination thereof, at a final concentration (x) of $0.4\ M < x \leqq 1.2\ M$.

* * * * *